(12) United States Patent
Engmark et al.

(10) Patent No.: US 7,668,597 B2
(45) Date of Patent: Feb. 23, 2010

(54) FEEDTHROUGH ARRAY FOR USE IN IMPLANTABLE MEDICAL DEVICES

(75) Inventors: David B. Engmark, Bethel, MN (US); Andrew J. Ries, Lino Lakes, MN (US)

(73) Assignee: Medtronic, Inc., Minneapolis, MN (US)

( * ) Notice: Subject to any disclaimer, the term of this patent is extended or adjusted under 35 U.S.C. 154(b) by 307 days.

(21) Appl. No.: 11/278,232

(22) Filed: Mar. 31, 2006

(65) Prior Publication Data

US 2007/0239223 A1 Oct. 11, 2007

(51) Int. Cl.
*A61N 1/00* (2006.01)
(52) U.S. Cl. ......................................... 607/37
(58) Field of Classification Search .................. 607/36, 607/37; 361/302
See application file for complete search history.

(56) References Cited

U.S. PATENT DOCUMENTS

| | | | |
|---|---|---|---|
| 4,644,943 A * | 2/1987 | Thompson et al. ............ 606/64 |
| 5,406,444 A * | 4/1995 | Selfried et al. ............... 361/302 |
| 5,535,097 A * | 7/1996 | Ruben et al. ................. 361/736 |
| 5,601,607 A * | 2/1997 | Adams ........................... 607/5 |
| 5,650,759 A * | 7/1997 | Hittman et al. .............. 333/182 |
| 5,870,272 A | 2/1999 | Seifried et al. |
| 5,905,627 A * | 5/1999 | Brendel et al. .............. 361/302 |
| 6,008,980 A * | 12/1999 | Stevenson et al. ........... 361/302 |
| 6,031,710 A * | 2/2000 | Wolf et al. .................... 361/302 |
| 6,052,623 A | 4/2000 | Fenner et al. |
| 6,076,017 A * | 6/2000 | Taylor et al. ................... 607/36 |
| 6,275,369 B1 * | 8/2001 | Stevenson et al. ........... 361/302 |
| 6,349,025 B1 * | 2/2002 | Fraley et al. ................. 361/302 |
| 6,414,835 B1 | 7/2002 | Wolf et al. |
| 6,453,551 B1 * | 9/2002 | Nordquist et al. .............. 29/862 |
| 6,490,148 B1 * | 12/2002 | Allen et al. .................. 361/302 |
| 6,519,133 B1 * | 2/2003 | Eck et al. ..................... 361/302 |
| 6,622,046 B2 * | 9/2003 | Fraley et al. ................... 607/36 |
| 6,660,116 B2 | 12/2003 | Wolf et al. |
| 6,768,629 B1 * | 7/2004 | Allen et al. .................. 361/302 |

* cited by examiner

*Primary Examiner*—Mark W Bockelman
*Assistant Examiner*—Roland Dinga (57) ABSTRACT

A feedthrough array for use in an implantable medical device is provided including an insulator, a plurality of conductive feedthrough pins extending through the insulator, and a ferrule including a flange extending inwardly from a ferrule sidewall along at least a majority of a length of a first ferrule side. A capacitor is disposed over the insulator and conductively coupled to the ferrule flange.

18 Claims, 8 Drawing Sheets

FEEDTHROUGH ARRAY FOR USE IN IMPLANTABLE MEDICAL DEVICES

TECHNICAL FIELD

The invention relates generally to implantable medical devices and, in particular, to configurations of a feedthrough array.

BACKGROUND

Electrical feedthroughs provide an electrical circuit path extending from the interior of a hermetically sealed housing of an implantable medical device (IMD) to the exterior of the housing. IMDs, such as cardiac pacemakers, implantable cardioverter defibrillators, neurostimulators, and physiological monitors, employ such electrical feedthroughs to make electrical connection with leads, electrodes or sensors located outside the IMD housing. A conductive path is provided through the feedthrough by a conductive feedthrough pin which is electrically insulated from the IMD housing. IMDs commonly operate in association with multiple leads, electrodes or sensors and thus feedthrough arrays including multiple feedthroughs have been developed.

IMDs can be susceptible to electromagnetic interference (EMI), which can interfere with proper IMD function. As such, capacitive filter arrays have been incorporated in the feedthrough arrays to filter each of the feedthroughs, shunting EMI at the entrance to the IMD. Examples of capacitive filtered feedthroughs for use with an IMD are generally disclosed in commonly assigned U.S. Pat. No. 5,870,272 (Seifried et al.) and U.S. Pat. No. 6,414,835 (Wolf, et al.), both of which patents are incorporated herein by reference in their entirety.

Feedthrough arrays used in IMDs must provide electrical connection across the IMD housing without compromising the hermeticity of the IMD housing. The feedthrough array generally includes a conductive ferrule that is welded to the IMD housing along an opening provided in the housing. Conductive feedthrough pins extending through the ferrule are supported and insulated from the ferrule by one or more ceramic insulators. A capacitive filter is electrically coupled to the feedthrough pins and the conductive ferrule to shunt EMI to the IMD housing serving as ground. A connector assembly is generally assembled over the ferrule and capacitive filter prior to welding the ferrule to the IMD housing. The connector assembly provides connector pads which facilitate electrical connection to the feedthrough pins. All of these components are assembled together in a manner that allows for leak testing of the feedthrough array to ensure that the feedthrough array will not compromise the hermeticity of the IMD housing.

DETAILED DESCRIPTION

In the following description, references are made to illustrative embodiments for carrying out the invention. It is understood that other embodiments may be utilized without departing from the scope of the invention. For purposes of clarity, the same reference numbers are used in the drawings to identify similar elements. Unless otherwise indicated, drawing elements are not shown to scale. In the description, the term "inwardly," when used with regard to a feedthrough assembly, generally refers to a direction toward the interior of an IMD. The term "outwardly" as used herein generally refers to a direction toward the exterior of an IMD.

Figure 1:
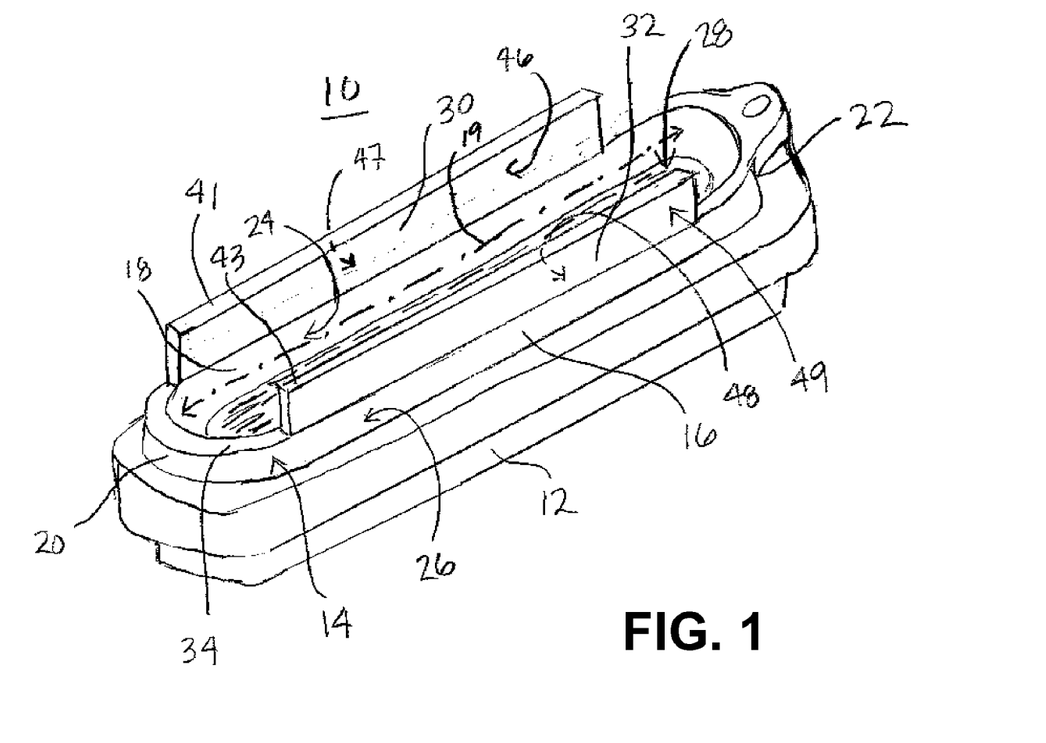
FIG. 1 is a perspective view of a ferrule used in a feedthrough array for an implantable medical device according to one embodiment of the invention.

FIG. 1 is a perspective view of a ferrule used in a feedthrough array for an implantable medical device according to one embodiment of the invention. Ferrule 10 is formed having a base portion 12 and a sidewall 14 extending inwardly from the base portion 12. Sidewall 14 includes an interior surface 24 and an exterior surface 26 separated by a top side 34. Sidewall 14 is formed as a continuous wall having opposing sides 16 and 18 and opposing ends 20 and 22. Ferrule 10 is provided with two flanges 30 and 32 having interior surfaces 46 and 48, exterior surfaces 47 and 49, and top surfaces 41 and 43, respectively. Interior surfaces 46 and 48, and optionally top surfaces 41 and 43, are provided for forming a conductive joint with a filtering capacitor as will be described in greater detail herein. A left-hand flange 30 extends inwardly from sidewall top side 34 along side 18, and a right-hand flange 32 extends inwardly from sidewall top side 34 along opposing side 16. Flange 30 extends along a majority of the length 19 of side 18 of sidewall 14. Likewise, flange 32 extends along a majority of the length of opposing side 16 of sidewall 14.

Ferrule 10 is fabricated from a conductive material such as niobium, titanium, platinum, molybdenum, zirconium, tantalum, vanadium, tungsten, iridium, palladium, or alloys thereof. Base portion 12 is adapted to be positioned in an opening of an IMD housing and welded to the IMD housing to electrically couple ferrule 10 to the housing without compromising the hermeticity of the housing. Interior surface 24 of sidewall 14 forms a cavity 28 for receiving a ceramic insulator which provides support and insulation to conductive feedthrough pins extending through ferrule 10.

Figure 2:
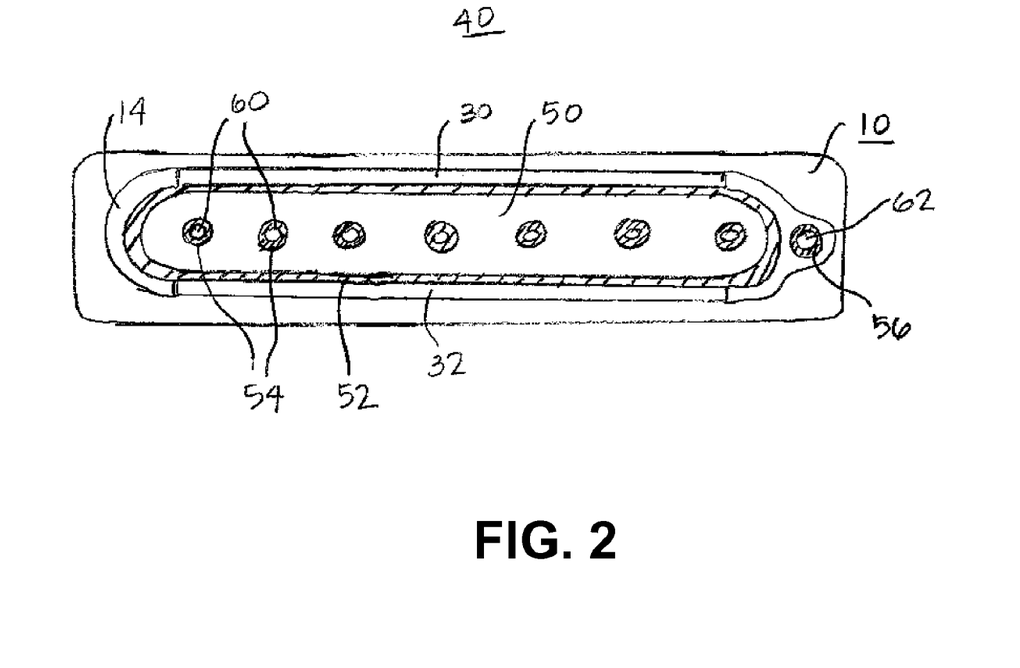
FIG. 2 is a top view of a braze assembly used in fabricating a feedthrough array.

FIG. 2 is a top view of a braze assembly used in fabricating a feedthrough array. Braze assembly 40 includes ferrule 10, a ceramic insulator 50 positioned in ferrule cavity 28 (shown in FIG. 1) formed by sidewall 14, one or more conductive feedthrough pins 60 extending through ceramic insulator 50 and a ground pin 62 coupled to ferrule 10. Each feedthrough pin 60 is coupled to ceramic insulator 50 by individual braze joints 54. Likewise, ground pin 62 is coupled to ferrule 10 by braze joint 56. Ceramic insulator 50 is coupled to ferrule 10 by braze joint 52. Feedthrough pins 60 and ground pin 62 may be gold sputtered to prevent oxide formation on the surface of the pins 60 that becomes conductively coupled to a capacitor and pin 62 that becomes conductively coupled to ferrule 10. Oxide formation would increase the contact resistance of the pins 60 and 62 and decrease the filtering or "insertion loss" of the feedthrough array.

Figure 3:
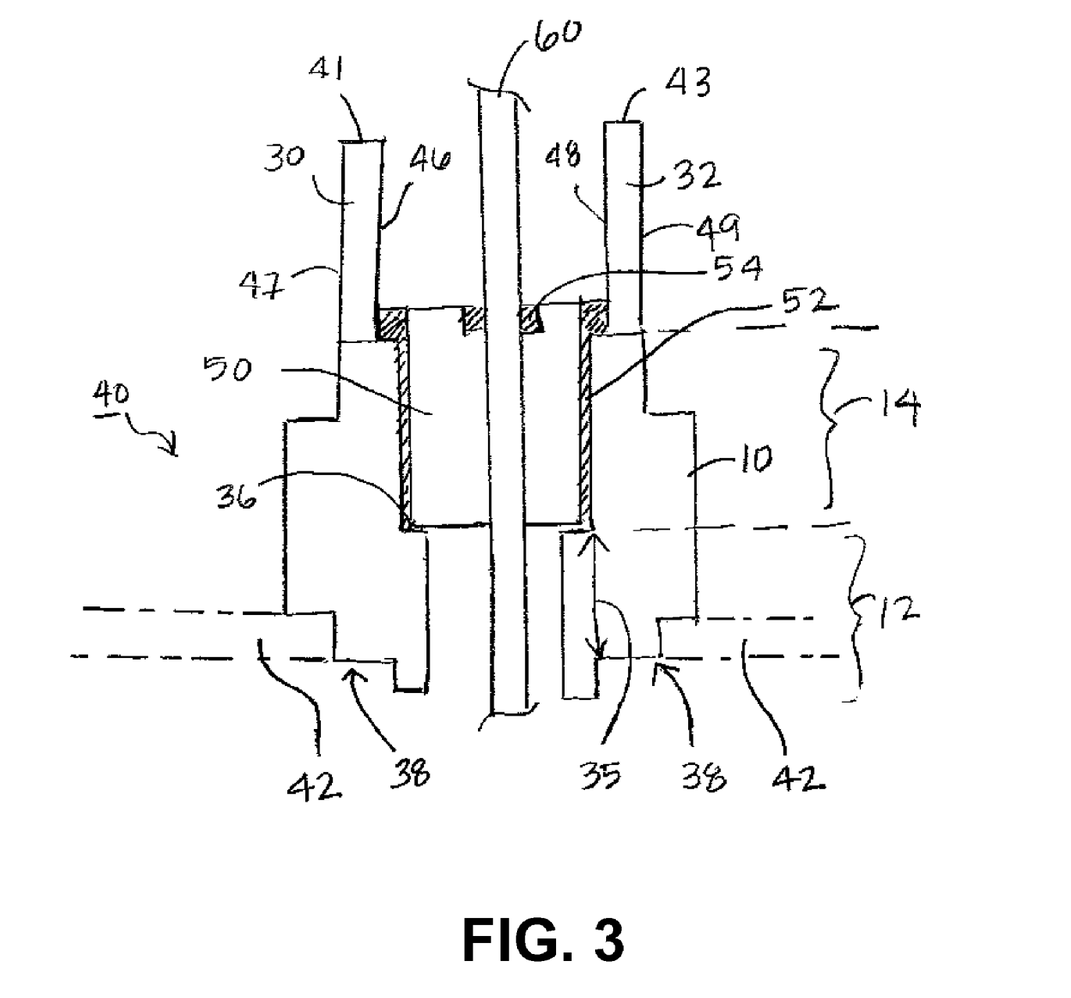
FIG. 3 is a sectional view of a braze assembly.

FIG. 3 is a sectional view of the braze assembly shown in FIG. 2. The base portion 12 of ferrule 10 includes a weld zone 38 which becomes welded to an IMD housing 42. Ferrule 10 is provided with an inwardly facing shelf 36 for interfacing with and supporting ceramic insulator 50. Ceramic insulator 50 is vulnerable to cracking when ferrule 10 is welded into an opening of IMD housing 42 along weld zone 38. In past practice, smaller, individual ceramic insulators have been provided for each feedthrough pin, which were less vulnerable to cracking during welding. In one embodiment of the present invention, ferrule base portion 12 is provided with a height that positions shelf 36, and therefore ceramic insulator 50, at a spaced apart distance 35 from weld zone 38. The spaced apart distance 35 between weld zone 38 and ceramic insulator 50 is controlled by specifying the corresponding height of base portion 12.

By moving shelf 36 further away from weld zone 38, by increasing the height of base portion 12, ceramic insulator 50 is less vulnerable to heating during welding processes that may lead to cracking of insulator 50. Flanges 30 and 32 provide added strength to ferrule 10 against twisting or distortion of ferrule 10 during welding. The added mechanical rigidity of ferrule 10 imparted by flanges 30 and 32 provides enhanced support to ceramic insulator 50 during welding, reducing the likelihood of fracture or cracking of ceramic insulator 50.

Any of the ferrule surfaces may be provided with an oxidative resistant coating to reduce contact resistances. In one embodiment, the interior surfaces 46 and 48 and the top surfaces 41 and 43 of flanges 30 and 32 are gold sputtered to promote good electrical connection with a capacitor.

Figure 4:
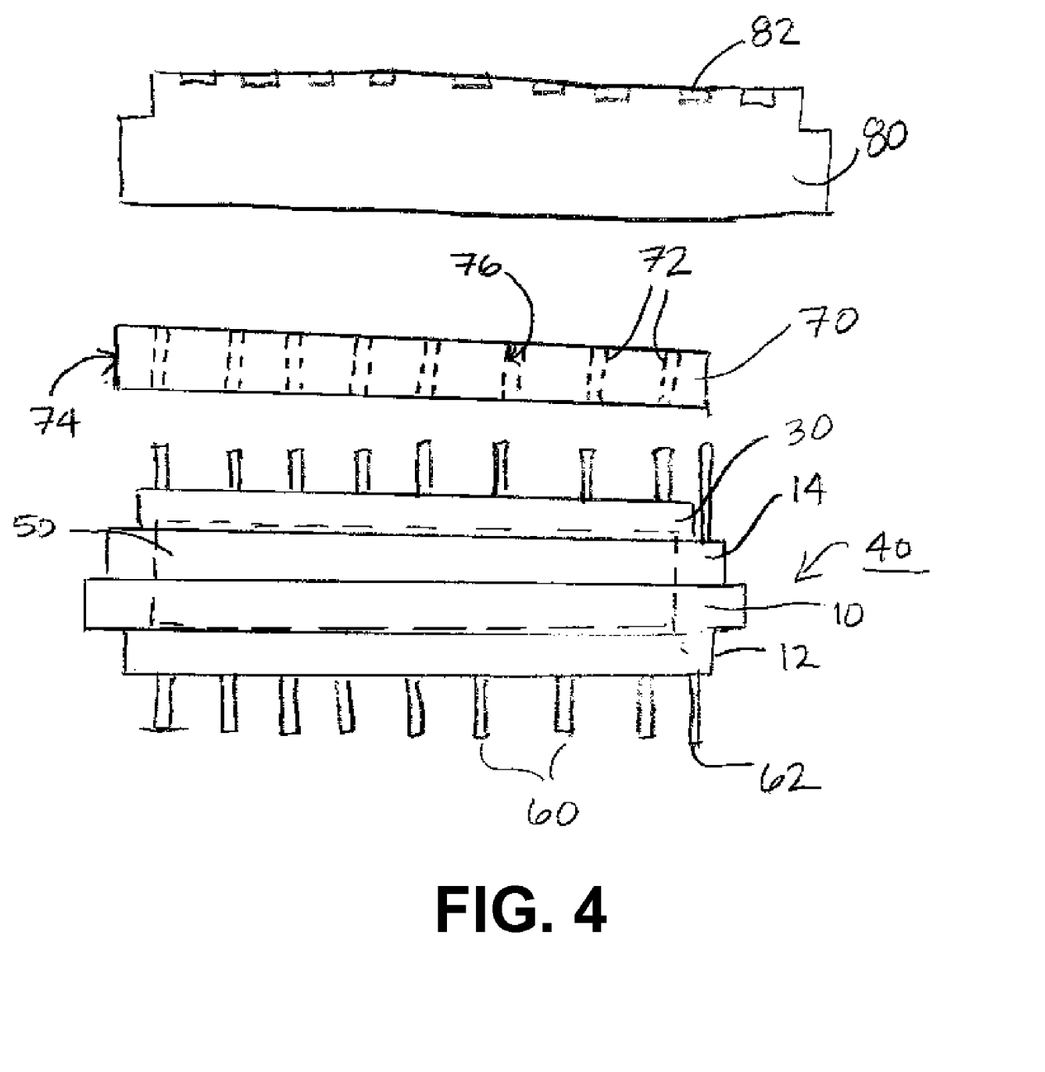
FIG. 4 is an exploded, side view of a feedthrough array.

FIG. 4 is an exploded, side view of a feedthrough array. A capacitor 70, provided with multiple feedthrough pin apertures 72, is advanced over feedthrough pins 60 and positioned over ceramic insulator 50 to provide filtering of each of feedthrough pins 60. While all of feedthrough pins 60 are shown positioned for extending through capacitor 70, it is recognized that in some embodiments the feedthrough array may include one or more unfiltered feedthrough pins that do not extend through capacitor 70. Capacitor 70 is typically terminated by the capacitor manufacturer by applying a metal coating on capacitor surfaces forming inner termination 76 along one or more feedthrough pin apertures 72 formed through capacitor 70 and outer termination 74 along the outer surfaces of capacitor 70. This coating typically includes silver or silver-palladium mixes and an organic binder-solvent mix. A conductive metallic material may be sputtered on the terminated surfaces 74 and 76 of capacitor 70 to reduce contact resistances on the capacitor surfaces.

A connector assembly 80 is positioned over capacitor 70 and braze assembly 40. Connector assembly 80 includes connector pads 82 for facilitating electrical connection to each of feedthrough pins 60 and ground pin 62. It is recognized that other components, such as spacers, insulating layers, and adhesive layers may be included between capacitor 70, ceramic insulator 50 and connector assembly 80.

A conductive epoxy is applied to the inner termination 76 of each aperture 72 of capacitor 70 to conductively couple each feedthrough pin 60 to capacitor 70. It is desirable that each of the braze joints 52 and 54 included in braze assembly 40 (as shown in FIG. 2) are leak testable to ensure that braze assembly 40 will not compromise the hermetically sealed IMD housing. As such, it is desirable to avoid application of an adhesive, such as epoxy, over ceramic insulator 50 for coupling capacitor 70 to ceramic insulator 50. Adhesive applied over any of the braze joints, intentionally or inadvertently due to flow of the adhesive, may mask a leak in a braze joint and prevent complete leak testability of the feedthrough array. Instead, capacitor 70 is coupled to braze assembly 40 by application of a conductive epoxy between the capacitor outer termination and the interior surfaces of ferrule flanges 30 and 32 and between the capacitor inner termination and the feedthrough pins.

Figure 5:
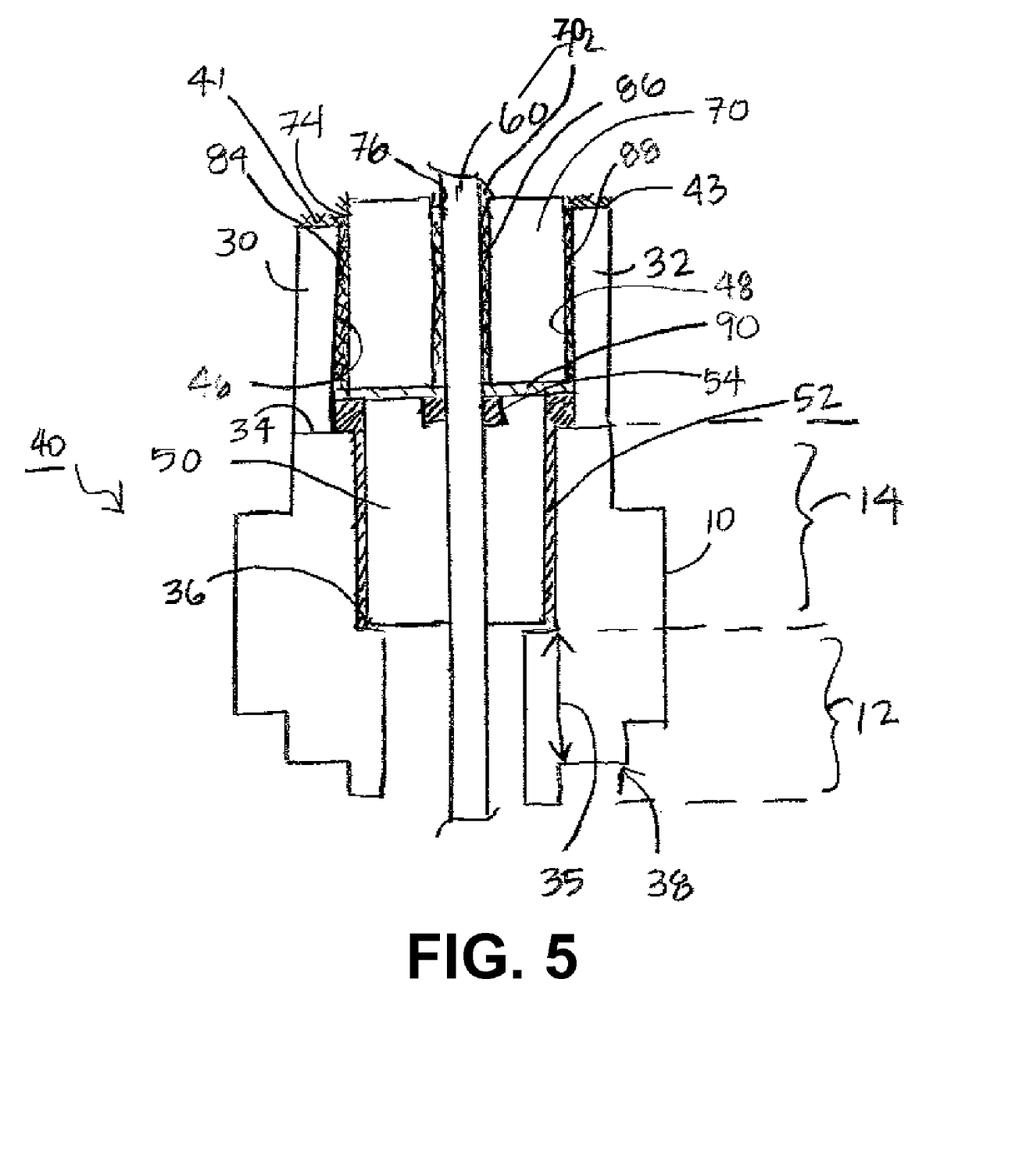
FIG. 5 is a sectional view of a capacitor assembled with a braze assembly.

FIG. 5 is a sectional view of a capacitor assembled with a braze assembly. Capacitor 70 is positioned between flanges 30 and 32, over insulator 50. Sidewall top surface 34 terminates below capacitor 70. Conductive joints 84 and 88 are formed between interior surfaces 46 and 48 of flanges 30 and 32 and the outer termination 74 of capacitor 70. Conductive joints 84 and 88 may be formed using a conductive adhesive, such as a conductive epoxy. Conductive joints 84 and 88 may extend over the top surfaces 41 and 43 by applying the conductive epoxy there over. Conductive epoxy is also applied to form a conductive joint 86 between the inner termination 76 of capacitor 70, which forms aperture 72, and feedthrough pin 60. By forming conductive joints 84 and 88 between outer termination 74 and flanges 30 and 32, and conductive joint 86 between inner termination 76 and pin 60, capacitor 70 is stably coupled to braze assembly 40 without applying epoxy over any of the braze joints 52 and 54. A spacer 90 may be provided between capacitor 70 and insulator 50 to provide added insulation or height adjustment to capacitor 70.

The large surface area provided by flange interior surfaces 46 and 48 for forming conductive joints 84 and 88 between ferrule 10 and capacitor 70 provide improved insertion loss of the feedthrough array. As indicated previously, interior surfaces 46 and 48 and top surfaces 41 and 43 may be sputtered with an oxidative resistant metal such as gold, to reduce contact resistances between flanges 30 and 32 and capacitor 70 to thereby improve insertion loss.

Figure 6:
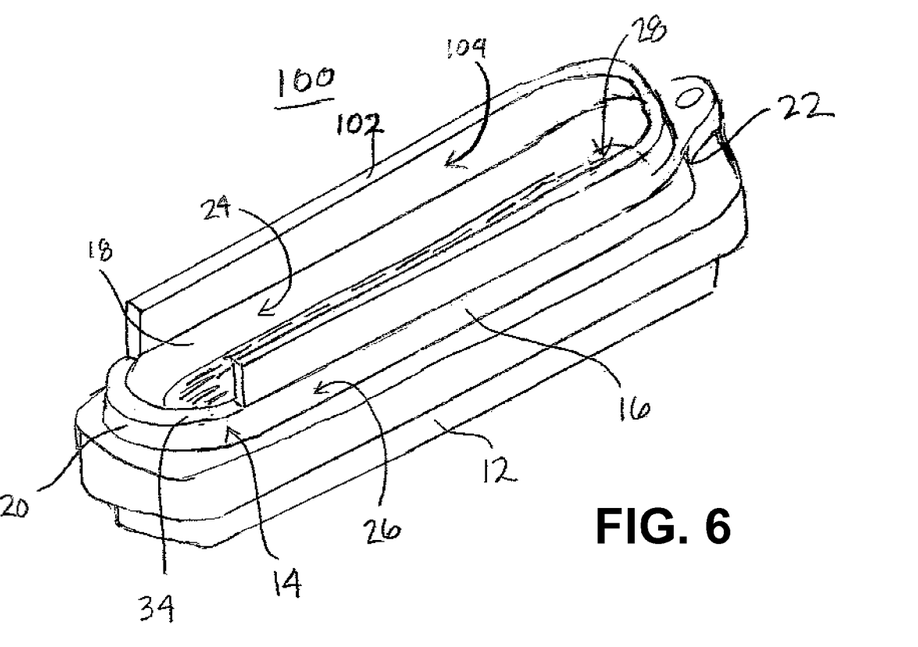
FIG. 6 is a perspective view of an alternative embodiment of a ferrule for use in a feedthrough array.

FIG. 6 is a perspective view of an alternative embodiment of a ferrule for use in a feedthrough array. Ferrule 100 includes a base portion 12 and sidewall 14 extending inwardly from base portion 12 as described previously in conjunction with FIG. 1. A generally U-shaped flange 102 is provided extending inwardly from top side 34 of sidewall 14 along at least a portion of each of sides 16 and 18 of sidewall 14 and along one end 22 of side wall 14. Flange 102 provides an interior coupling surface 104 for forming a conductive joint with the outer termination of a capacitor included in a feedthrough array. The conductive joint may extend along the entire interior coupling surface 104 or any portion thereof. For example, in some embodiments a capacitor may be conductively joined to the interior coupling surface 104 only along the flange portions extending from sidewall sides 16 and 18. In other embodiments, a conductive joint between flange 102 and the capacitor may include the flange portion extending from sidewall end 22. Flange 102 provides structural rigidity to ferrule 100 to better withstand welding without twisting or distortion, thereby providing better support to a ceramic insulator inserted in cavity 28 and thereby reducing the likelihood of ceramic insulator cracking. Flange 102 also provides a large interior surface 104 for forming a conductive joint with a filtering capacitor, improving insertion loss of the feedthrough array.

Figure 7:
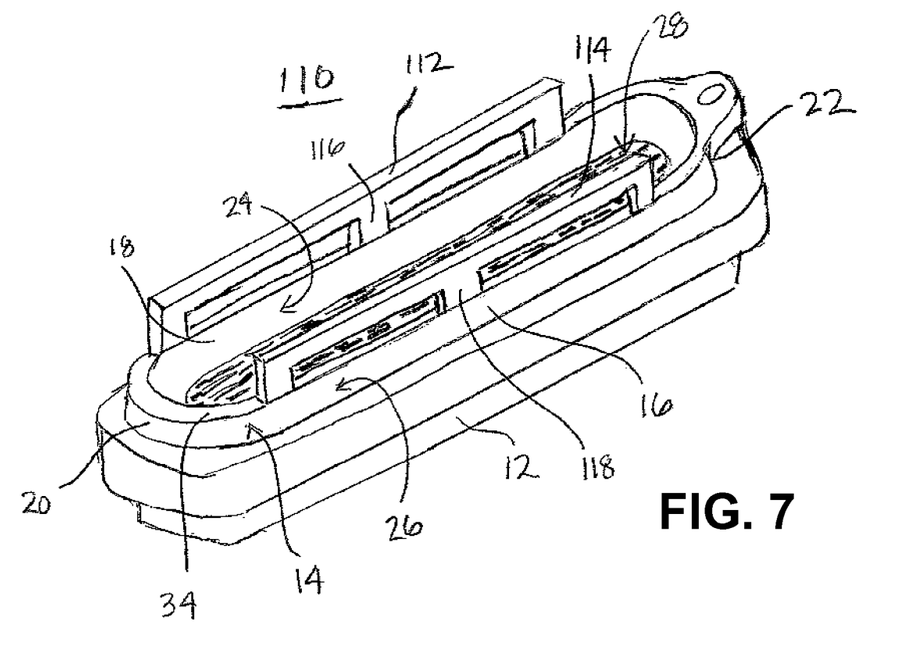
FIG. 7 is a perspective view of yet another embodiment of a ferrule for use in a feedthrough array.

FIG. 7 is a perspective view of yet another embodiment of a ferrule for use in a feedthrough array. Ferrule 10 shown previously in FIG. 1 is provided with flanges 30 and 32 formed as solid pieces of material extending from sidewall 14. Flanges provided for forming a relatively large surface area, conductive joint between a capacitor and a ferrule and/or for improving the rigidity of the ferrule may alternatively be formed as non-solid pieces which include one or more structures such as ribs, perforations or other structures that define openings in the flange. For example, ferrule 110 is provided with flanges 112 and 114 extending inwardly from top surface 34 of sidewall 14 wherein each flange 112 and 114 are provided with one or more ribs 116 and 118, respectively. Flanges 112 and 114 extend along a majority of the length of sides 16 and 18.

Figure 8:
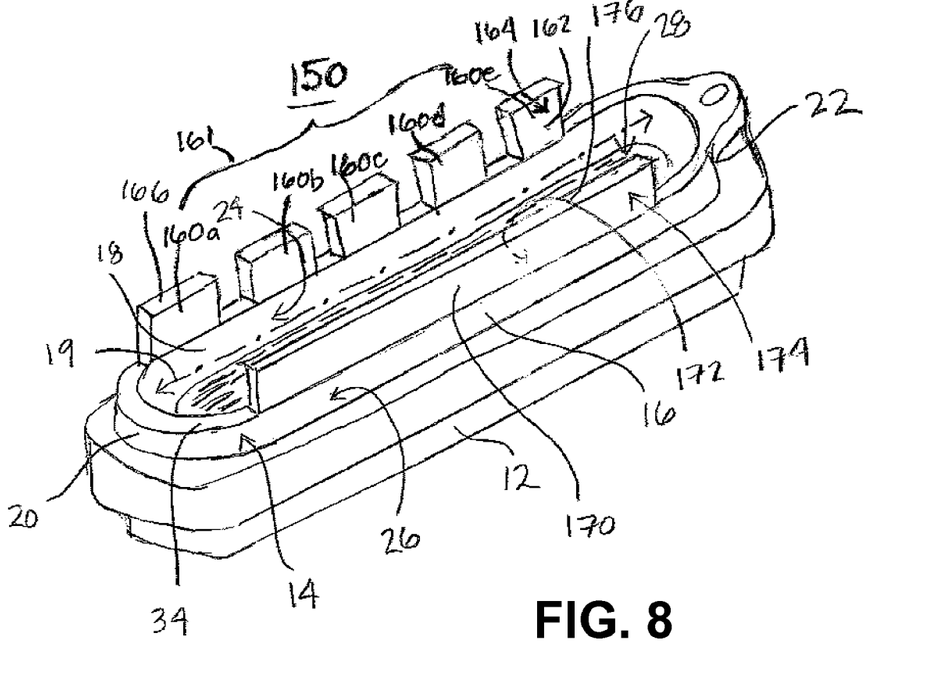
FIG. 8 is a perspective view of a ferrule having a flange formed from multiple individual structures extending inwardly from the ferrule sidewall.

FIG. 8 is a perspective view of a ferrule having a flange formed from multiple individual structures extending inwardly from the ferrule sidewall. Capacitor connection tabs 160a through 160e individually extend less than a majority of the length 19 of ferrule sidewall side 18. Collectively, connection tabs 160a through 160e form a flange 162 extending a total distance of at least a majority of the length 19 of side 18. A conductive joint is formed between the outer termination of the capacitor and the interior surface 162, and optionally the top surface 166, of each of connection tabs 160a through 160e.

A second flange 170 is shown extending along opposing side 16, for at least a majority of the length 19 of side 16. Flange 170 includes interior surface 172, top surface 176 and exterior surface 174. Interior surface 172 and optionally top surface 176 are used in forming a conductive joint with the outer termination of the capacitor. Any of the flange surfaces 172, 174 and 176 and any of the connection tab interior surfaces 162, top surfaces 166 and exterior surfaces 164 may be gold sputtered or otherwise surface enhanced for promoting good electrical connection. In an alternative embodiment, one or more connection tabs may also be provided along opposing side 16.

As illustrated by the various embodiments presented herein, a feedthrough array ferrule is provided having at least one flange extending along at least a majority of the length of one side of the ferrule sidewall. The flange may be formed as a solid structure, a non-solid structure, or a plurality of individual structures referred to herein in one illustrative embodiment as "capacitor connection tabs." Further it is recognized that when the flange is formed from individual structures, the individual structures may be solid or non-solid structures or a combination of both.

The flange provides, among other things, added rigidity to the ferrule for supporting the insulator and/or a relatively large surface area for forming a conductive joint between the ferrule and the capacitor for improving insertion loss of the feedthrough array. It is recognized that numerous configurations may be conceived by one having skill in the art and the benefit of the teachings provided herein for providing a feedthrough array having a ferrule with a combination of one or more flanges, and optionally one or more connection tabs, extending inwardly from one or both ferrule sidewall sides and optionally one or both ferrule sidewall ends.

Figure 9:
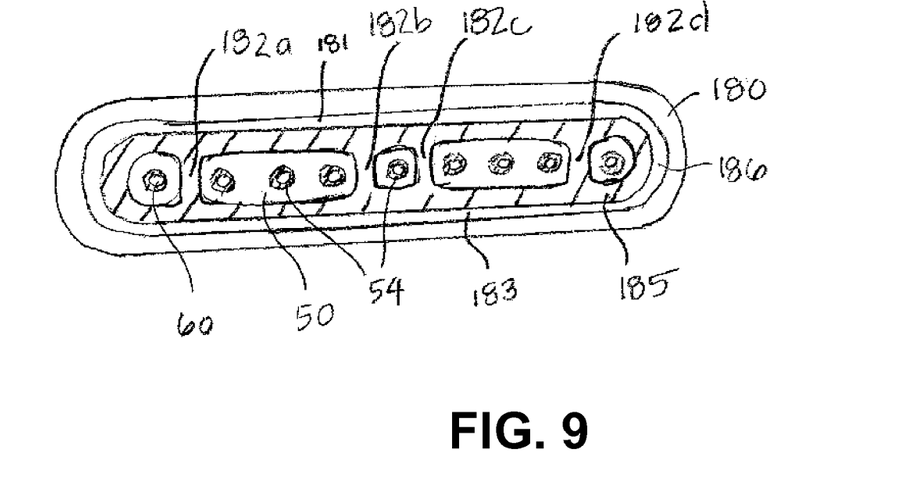
FIG. 9 is a bottom view of a braze assembly including a ferrule provided with base cross beams.

FIG. 9 is a bottom view of a braze assembly including a ferrule provided with base cross beams. Ferrule 180 is shown having a bottom surface 185 including multiple cross beams 182a through 182d for adding structural support to ferrule 180. Feedthrough pins 60 extend through ferrule 180, through openings formed between cross beams 182a through 182d, and through single ceramic insulator 50. Braze joints 54 are formed between feedthrough pins 60 and insulator 50 as described previously. It is recognized that any number of cross beams may be provided extending across base portion 186, between base portion sides 181 and 183.

Figure 10:
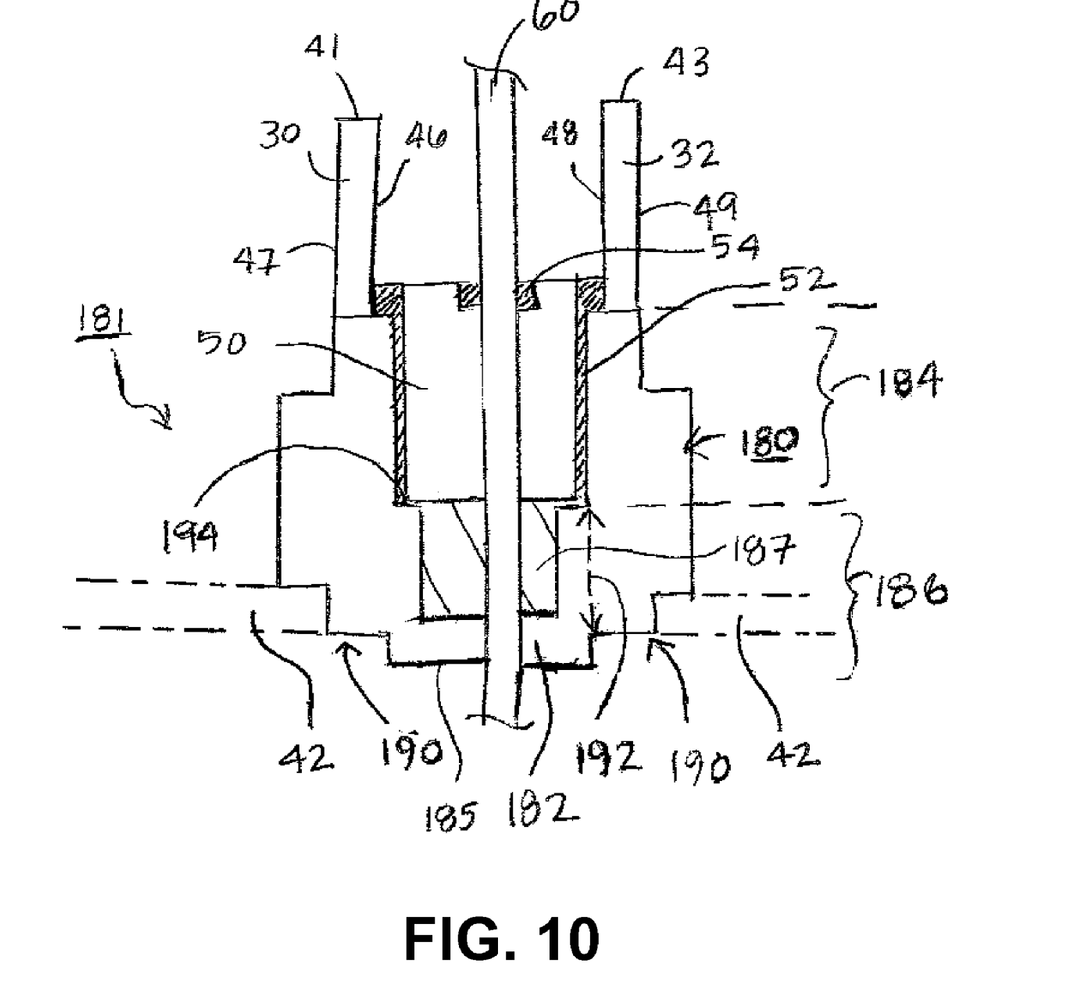
FIG. 10 is a sectional view of a braze assembly including a ferrule with base cross beams.

FIG. 10 is a sectional view of a braze assembly including a ferrule with base cross beams. A cross beam 182 extends across base potion 186 forming a bottom surface 185 of base 186. Cross beam 182 provides added support to ferrule 180 during welding of ferrule 180 to IMD housing 42 along weld zone 190. Cross beam 182 acts to reduce twisting and distortion of ferrule 180 which may otherwise lead to cracking of insulator 50. A non-conductive joint 187 is formed between cross beam 182 and insulator 50 by applying a non-conductive adhesive, such as a non-conductive epoxy, between cross beam 182 and insulator 50.

Figure 11:
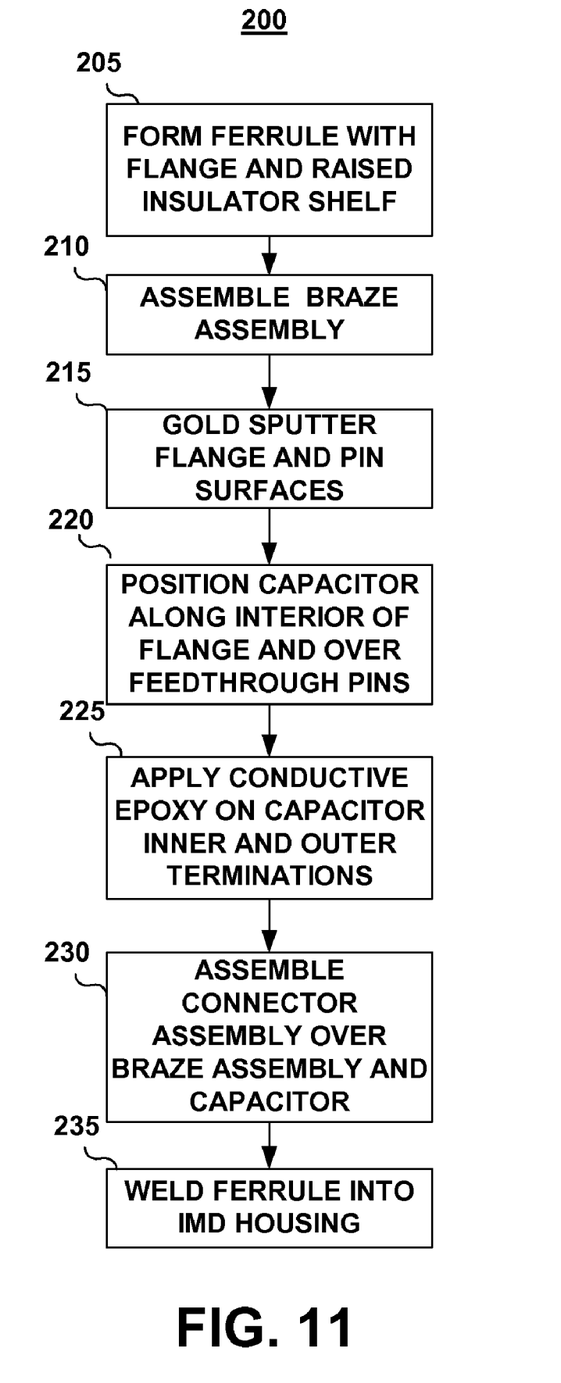
FIG. 11 is a flow chart summarizing steps included in a method for manufacturing a feedthrough array according to one embodiment of the invention.

FIG. 11 is a flow chart summarizing steps included in a method for manufacturing a feedthrough array according to one embodiment of the invention. At block 205, a ferrule is formed with one or more flanges extending inwardly from the ferrule sidewall providing a relatively large interior surface area for forming a conductive joint with a filtering capacitor. At least one flange extending along at least a majority of one side of the ferrule sidewall is provided. The flange may extend further, along one or both ends of the ferrule sidewall and may continue along a portion of the second side of the ferrule sidewall. The ferrule flange(s) may be formed as: a solid structure; a non-solid structure, i.e., a structure having ribs, perforations, or other features that define openings or gaps in the flange(s); or from multiple connection tabs or other individual structures that collectively form a flange extending inwardly along at least a majority of at least one side of the ferrule sidewall.

The ferrule may also be formed (as indicated at block 205) having a base height that separates the insulator shelf from the welding zone by a spaced-apart distance corresponding to the base portion height.

At block 210, the ferrule is assembled with one or more feedthrough pins and a ceramic insulator to form a braze assembly. Braze joints are formed between the feedthrough pins and the ceramic insulator and between a ground pin and the ferrule. A braze joint is also formed between the ceramic insulator and the ferrule sidewall.

At block 215, the ferrule flanges are provided with an oxidative resistant coating, such as a gold sputtered coating, to promote good electrical connection between the ferrule flange(s) and the capacitor. Any surfaces, e.g., interior, exterior, and top of the flange(s), may be gold sputtered. The feedthrough pins are also provided with an oxidative resistant coating, such as a gold sputtered coating, over the portions to be conductively joined to the capacitor to promote good electrical connection between the feedthrough pins and the capacitor.

The capacitor is positioned over the feedthrough pins at block 220. The capacitor is positioned along the interior surface of the ferrule flange(s). At block 225, a conductive adhesive, such as conductive epoxy, is applied to the capacitor inner and outer terminations. A conductive joint is formed between the capacitor outer termination and the flange interior surface and optionally the flange top surface. Conductive joints are formed between each of the feedthrough pins and the capacitor inner termination.

At block 230 a connector assembly is assembled over the capacitor and braze assembly to form the feedthrough array. The feedthrough array is hermetically and electrically coupled to an IMD housing at block 235, for example by welding the ferrule base portion along an opening of the IMD housing. It is understood that the manufacturing method 200 may include leak testing steps to ensure that the feedthrough array does not compromise the hermeticity of the IMD housing.

Thus, a feedthrough array and method for fabrication have been presented in the foregoing description with reference to specific embodiments. It is appreciated that various modifications to the referenced embodiments may be made without departing from the scope of the invention as set forth in the following claims.

The invention claimed is:

1. A feedthrough array for use in an implantable medical device, comprising:
   an insulator;
   a plurality of conductive feedthrough pins extending through the insulator;
   a ferrule comprising a base portion adapted to be electrically and hermetically coupled to a housing of the medical device, a sidewall extending inwardly from the base portion, the sidewall including opposing first and second ferrule sides extending between opposing first and second ferrule ends forming a cavity there between for receiving the insulator, and at least one cross beam that extends between the opposing first and second ferrule sides, the at least one cross beam being located between two of the plurality of conductive feedthrough pins;
   a flange extending inwardly from the ferrule sidewall along at least a majority of a length of the first ferrule side, the flange having an interior surface, a top surface, and an exterior surface;
   a capacitor disposed over the insulator, the capacitor having an inner termination and an outer termination;
   a first conductive joint formed between the capacitor outer termination and the flange; and
   a plurality of second conductive joints formed between the capacitor inner termination and the plurality of conductive feedthrough pins.

2. The feedthrough array of claim 1 further comprising a second flange extending inwardly from the ferrule sidewall along a portion of a length of the second ferrule side.

3. The feedthrough array of claim 2, wherein the first flange and the second flange are substantially straight.

4. The feedthrough array of claim 1 wherein the flange further extends along one of the first ferrule end and the second ferrule end.

5. The feedthrough array of claim 4 wherein the flange further extends along a portion of the second ferrule side.

6. The feedthrough array of claim 1 wherein the flange being one of a solid structure, a non-solid structure, and a plurality of individual structures.

7. The feedthrough array of claim 6 wherein the flange includes one or more ribs.

8. The feedthrough array of claim 1 wherein the first conductive joint being formed along at least one of the flange interior surface and the flange top surface.

9. The feedthrough array of claim 1 further comprising an oxidative resistant coating applied to at least one of the flange interior surface, the flange exterior surface and the flange top surface.

10. The feedthrough array of claim 1 wherein the base portion includes:
    an insulator shelf for supporting the insulator,
    and a weld zone for coupling the base portion to the IMD housing, wherein the weld zone and the insulator shelf are separated by a distance corresponding to the base portion height.

11. The feedthrough array of claim 10 wherein the distance separating the insulator shelf from the weld zone being about 0.032".

12. The feedthrough array of claim 1 wherein the flange being a generally U-shaped flange that extends inwardly along at least a portion of the first ferrule side and the second ferrule side.

13. A feedthrough array for use in an implantable medical device, comprising:
    an insulator;
    a plurality of conductive feedthrough pins extending through the insulator; and
    a ferrule comprising:
       a base portion adapted to be electrically and hermetically coupled to a housing of the medical device,
       a sidewall extending inwardly from the base portion, the sidewall including opposing first and second ferrule sides extending between opposing first and second ferrule ends forming a cavity there between for receiving the insulator,
       at least one cross beam that extends between the opposing first and second ferrule sides, the at least one cross beam being located between two of the plurality of conductive feedthrough pins, and
       a flange extending inwardly from the ferrule sidewall along at least a majority of a length of the first ferrule side, the flange having an interior surface, a top surface, and an exterior surface.

14. The feedthrough array of claim 13, further comprising a second flange extending inwardly from the ferrule sidewall along a portion of a length of the second ferrule side.

15. The feedthrough array of claim 14, wherein the first flange and the second flange are substantially straight.

16. The feedthrough array of claim 13, wherein the flange being a generally U-shaped flange that extends inwardly along at least a portion of the first ferrule side and the second ferrule side.

17. The feedthrough array of claim 13, wherein the at least one cross beam is on an outwardly facing surface of the ferrule.

18. The feedthrough array of claim 13, wherein the plurality of conductive feedthrough pins are in a row, and the at least one cross beam transects the row such that the feedthrough pins extend through openings adjacent to the at least one cross beam.

* * * * *